United States Patent
Holman et al.

(10) Patent No.: US 6,258,195 B1
(45) Date of Patent: Jul. 10, 2001

(54) MULTI-CORD FUSING MANUFACTURING PROCESS FOR CATHETER MEMBERS

(75) Inventors: Thomas J. Holman, Minneapolis; Gregory K. Olson, Elk River; Philip J. Ebeling, Savage, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/272,510

(22) Filed: Mar. 19, 1999

(51) Int. Cl.⁷ ....................................... B32B 31/00
(52) U.S. Cl. .................. 156/166; 156/180; 156/296; 156/305; 156/308.4; 156/308.6; 156/272.2; 156/275.1; 604/524; 604/527; 604/526
(58) Field of Search ................... 604/280, 282, 604/524, 526, 527; 156/166, 180, 296, 308.4, 149, 245, 272.2, 273.3, 275.1, 305, 308.6

(56) References Cited

U.S. PATENT DOCUMENTS

| | | | |
|---|---|---|---|
| 3,007,497 | * 11/1961 | Shobert | 156/149 |
| 3,553,341 | 1/1971 | Hureau . | |
| 3,618,613 | 11/1971 | Schulte . | |
| 3,724,985 | 4/1973 | Burlis et al. . | |
| 3,919,026 | 11/1975 | Mizutani et al. . | |
| 3,933,960 | 1/1976 | Cameron et al. . | |
| 3,997,382 | 12/1976 | Tanaka . | |
| 4,093,693 | 6/1978 | Lemelson . | |
| 4,277,432 | 7/1981 | Woinowski . | |
| 4,321,226 | 3/1982 | Markling . | |
| 4,385,635 | * 5/1983 | Ruiz | 604/280 |
| 4,516,972 | * 5/1985 | Samson | 604/282 |
| 4,577,543 | * 3/1986 | Wilson | 87/11 |
| 4,764,324 | 8/1988 | Burnham . | |
| 4,888,146 | 12/1989 | Dandeneau . | |
| 5,019,057 | * 5/1991 | Truckai | 604/282 |
| 5,092,950 | * 3/1992 | Spoo et al. | 156/180 |
| 5,156,785 | 10/1992 | Zdrahala . | |
| 5,222,949 | 6/1993 | Kaldany . | |
| 5,248,305 | 9/1993 | Zdrahala . | |
| 5,251,640 | 10/1993 | Osborne . | |
| 5,316,706 | 5/1994 | Muni et al. . | |
| 5,334,171 | 8/1994 | Kaldany . | |
| 5,451,209 | * 9/1995 | Ainsworth et al. | 604/282 X |
| 5,456,674 | 10/1995 | Bos et al. . | |
| 5,472,435 | 12/1995 | Sutton . | |
| 5,639,409 | 6/1997 | van Muiden . | |
| 5,733,496 | 3/1998 | Avellanet . | |
| 5,736,094 | 4/1998 | van Muiden . | |
| 5,738,923 | 4/1998 | Ko et al. . | |
| 5,868,718 | 2/1999 | Pepin et al. . | |
| 5,874,032 | 2/1999 | Zdrahala . | |

FOREIGN PATENT DOCUMENTS

| | | | | |
|---|---|---|---|---|
| 2204888 | * | 1/1995 | (GB) | 156/149 |
| 7-9597 | * | 1/1995 | (JP) | 156/149 |

* cited by examiner

*Primary Examiner*—Jeff H. Aftergut
(74) *Attorney, Agent, or Firm*—Crompton, Seager & Tufte, LLC

(57) ABSTRACT

Medical tubing having a wall formed of multiple strands bonded together. One method for making the tubing utilizes multiple spools containing polymeric strands disposed about a central mandrel, with the strands aligned with and disposed evenly about the mandrel, with both mandrel and strands entering a die or other bonding device. Adjacent strands are bonded together to form a tube wall, the tube preferably having at least one lumen therethrough. Adjacent strands are lightly bonded in some embodiments and highly bonded in others. Bonding can be accomplished using heat, solvent welding, or adhesive. The strands making up the tube wall can be formed of materials differing between strands. One use of the tubing is for constructing angioplasty catheters.

14 Claims, 2 Drawing Sheets

Fig. 1
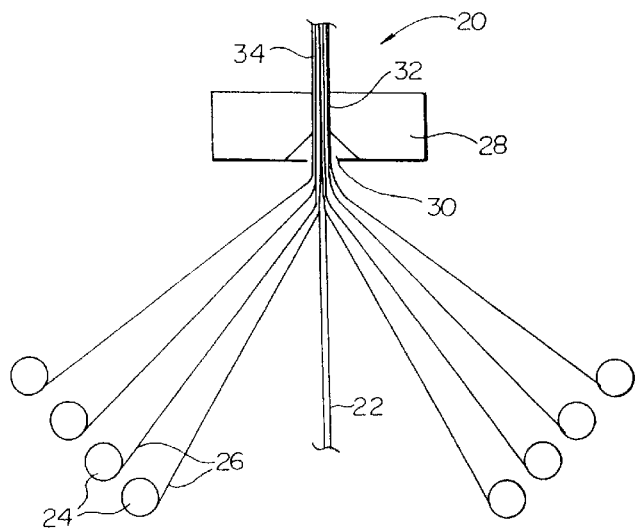
Fig. 2
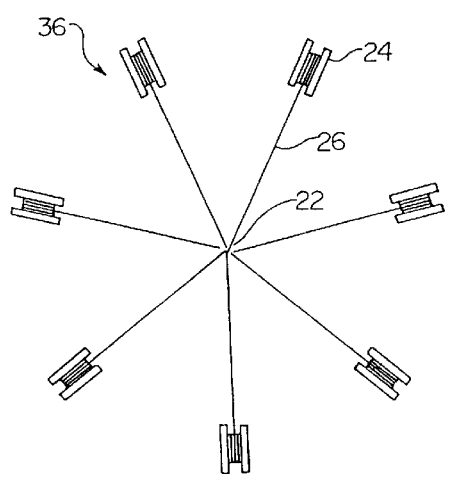
Fig. 3
Fig. 4
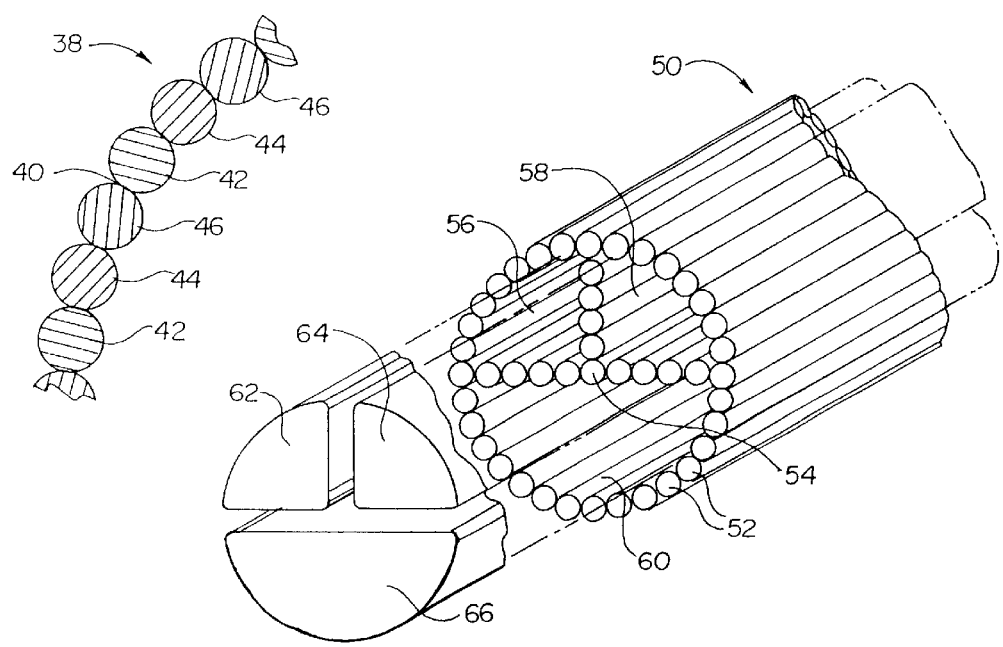

MULTI-CORD FUSING MANUFACTURING PROCESS FOR CATHETER MEMBERS

FIELD OF THE INVENTION

The present invention is related generally to medical device tubular members and methods for manufacturing the tubular members. More specifically, the present invention relates to methods for making catheter tubular members including aligning multiple strands of material and fusing adjacent strands together to form a tube.

BACKGROUND OF THE INVENTION

The use of tubing and tubular members is ubiquitous in medical devices. In many tube-containing devices, such as intravascular catheters, the physical characteristics of the tubing are of great importance. For example, in catheters used in percutaneous transluminal coronary angioplasty (PTCA), the catheter tubing must extend from the patient's groin, through the femoral artery, over the aortic arch, into a coronary ostium, thereafter through tortuous vessel passages and into a secondary or tertiary coronary vessel within the heart. The tubing must be sufficiently flexible to track the often-tight turns through the vessels, yet capable of being pushed through the coronary vessels from a location near the groin. The tubing must also be capable of transmitting rotational forces applied near the groin into tip rotation near the heart.

The above requirements for catheters are often referred to as trackability, pushability, and torqueability. Meeting these requirements is complicated by a further requirement of having a small profile or outside diameter, so as to be able to pass through a small lumen, such as a remote coronary vessel of small inside diameter. Catheter tubing has often been made using variations of common tubing manufacture processes such as extrusion. Polymer is sometimes extruded over a mandrel, wrapped with wire or braid, and extruded over in a second pass, covering the braid. Such a process can impart a lubricious and/or strong inner surface, a strong intermediate braid, and a lubricious outer surface. The use of extrusion to form medical tubing commonly results in a homogenous tube wall consisting of melted polymer which is substantially uniform in orientation and composition.

What would be desirable is a simple method for making medical tubing that results in a tube having improved axial strength and pushability. It is further desired to have a method of manufacture in which the polymeric tube wall can incorporate varying or selected circumferential portions over the tube length with non-homogenous materials and properties. What would be further desirable is a method for making medical tubing having shapes and wall structures not possible using conventional extrusion methods.

SUMMARY OF THE INVENTION

The present invention provides improved medical tubular members or tubes formed of multiple strands bonded together. One use of such tubes is in construction of angioplasty catheters. One method utilizes multiple spools containing strand material disposed about a central mandrel, with the strands aligned with and disposed evenly about the mandrel. Both the mandrel and aligned strands then enter a die or other bonding device. Adjacent strands are bonded together to form a tube, with the tube preferably having at least one lumen therethrough. The strands making up portions of the tube wall can vary in composition from other strands making up other portions of the tube wall. The bonded strand tube walls can provide tubes having improved handling characteristics relative to tube walls formed from extruded polymer.

One method according to the present invention uses heat to fuse adjacent strands together by melting only the exterior surface or top layer of the strands. The resulting tube walls can retain much of the fine structure of the original strands. Another method uses heat to fuse adjacent strands together by melting a substantial portion of the strand well into the strand interior. The resulting tube walls can have a smoother surface, can be molded to have less of the structure of the original strands, and can have more shape dictated by polymer flow and the shape of the forming mandrel and die. Another method utilizes adhesive to bond the strands together. Yet another method utilizes solvent welding to fuse adjacent strands. Still another method includes UV curable material within the strands and exposure to UV light to bond the strands together.

Strands used to form the tube are preferably formed of polymeric materials suitable for bonding to adjacent strands. One class of strands includes metallic wire coated with polymeric material. Another class of strands includes fibrous material coated with polymeric material. Yet other strands are formed of multiple filaments. In another embodiment, the strands may be coated as they pass into or within the bonding device, rather than being pre-coated.

After bonding adjacent strands into a tube, some embodiments include further processing. One method includes extrusion of polymer over the multi-strand tube. Another method includes applying a metallic coating over the tube by a method such as sputter coating. Yet another method includes winding a strand about the tube which can increase the collapse strength of the tube.

BRIEF DESCRIPTION OF THE DRAWINGS

FIG. 1 is a highly diagrammatic top view of a system for making medical tubing including multiple spools feeding strands into a heated die or other bonding device;

FIG. 2 is a highly diagrammatic end view of a system having seven spools feeding strands into a bonding device;

FIG. 3 is a fragmentary, transverse, cross-sectional view of a tube wall section including lightly fused strands;

FIG. 4 is a fragmentary, perspective view of a tube including three lumens having tube walls formed of strands lightly fused with the aid of three mandrels;

DETAILED DESCRIPTION OF THE INVENTION

Figure 7:
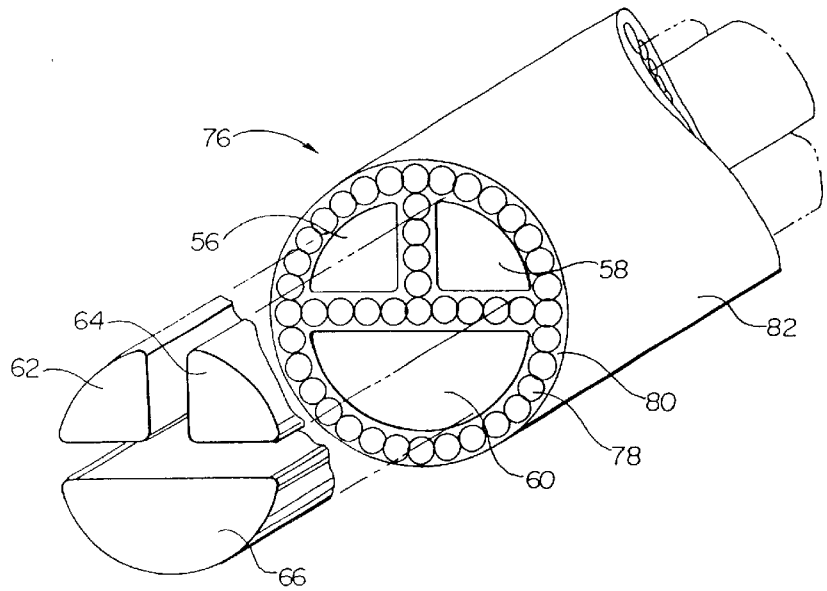
FIG. 7 is a fragmentary, perspective view of a tube wall section including three lumens having tube walls formed of strands bonded together with the aid of a filling and/or bonding agent and three mandrels.

FIG. 1 illustrates a portion of a tube forming system 20 including a central mandrel or form 22, and several spools 24 containing strands 26. Only eight spools are shown to simplify the drawing. In a preferred embodiment, more than eight spools are used. Strands 26 can be fed to a die or bonding device 28, being funneled or concentrated in a concentrating or aligning region 30 of die/bonding device 28. In the embodiment illustrated, die 28 includes a heating region 32 for fusing strands 26 together. In other embodiments, region 32 may include an injection port or multiple injection ports for injecting a bonding agent to aid in bonding strands 26 together. In still other embodiments, region 32 may include an injection port or multiple injection ports for adding a solvent used in solvent welding the strands together. Exiting die 28 is a finished or partially finished tube 34. In some embodiments, a cooling or curing region is included downstream of die. Tube 34 is subsequently wound around a take-up spool in some embodiments. The central mandrel 22 can also be heated to fuse strands proximate the surface thereof. The central mandrel 22 can include a coil inside which is heated by RF field resistance.

Referring now to FIG. 2, an alternative tube forming system 36 is illustrated from an end view, having only seven spools to simplify the drawing. Spools 24 are shown disposed evenly about central mandrel 22, and illustrate the strands 26 fed or converged about the mandrel 22. In a preferred embodiment, more spools than seven are used to form the resulting tube.

Referring now to FIG. 3, a tube wall section 38 is illustrated, formed of a plurality of lightly fused or bonded strands. As indicated by the cross-hatching, different types of strands are included in wall section 38, including first strands 42, second strands 44, and third strands 46. By fusing or bonding strands formed of different materials, the composite tube wall can have overall tube properties imparted from strands not necessarily having all of these properties present in a single strand. For example, stiffness can be imparted to the overall tube by fusing one or more strands formed of a stiffer polymeric material or a bondable polymer covering a metallic wire. As indicated at 40, the strands of tube wall section 38 are only lightly fused together. The strands retain much of their original round shape and are bonded together where the strands touch along the strand circumferences. In this embodiment, the strand is not melted to any substantial depth during formation of the tube so that the strand shape is retained and very little diffusion of material between strands occurs.

Referring now to FIG. 4, a tube 50 is illustrated, including a plurality of strands 52 bonded together into a tube including a first lumen 56, a second lumen 58, and a third lumen 60. The three lumens are separated by a "T" shaped element 54 formed of strands fused or otherwise bonded together. In another embodiment, the T shaped element is formed externally using conventional techniques and is supplied to the strand-bonding device. Extending through the three lumens are a first mandrel 62, a second mandrel 64, and a third mandrel 66. The mandrels illustrate one apparatus that can be used to form both multiple lumens, lumen walls and the external tube walls into the desired shape and to form internal walls within the tube. In one embodiment, a single, preferably round, mandrel is used, corresponding to a single lumen.

One method for making a tube includes pulling the multiple strands from their respective spools, over a central mandrel or core wire, and through an aligner. The strand-covered mandrel can then be received within a die. The strands can thus be disposed between an inner central mandrel and a surrounding die surface. The inner mandrel and outer die can both be heated to a temperature sufficient to bond the strands together. The central mandrel can thus serve both to fuse or otherwise bond the strands together and to maintain a lumen within the bonded strands forming the tube. One method utilizes a single core wire as the mandrel. A continuous core wire having a continuous layer of strands formed over the core wire can be fused together into a tube using heat applied from within by the core wire and applied from without by a die. The tube formed over the core wire can be wound onto a spool and the core wire removed at a later processing stage.

Another method utilizes a shorter, fixed length mandrel corresponding to the length of the tube to be formed. The mandrel can have multiple strands aligned with the mandrel and surrounding the mandrel. The strand-covered mandrel can then be drawn through a die until the entire mandrel has been pulled through the die and fused. The tube can be cut after the mandrel has exited the die and the mandrel removed from within the newly formed tube. In some methods, the mandrel is used again to form another tube. In one method, the mandrel is tapered, having decreasing outer dimensions over its length. The tapered mandrel can be used to form a tube having either a decreasing lumen inside diameter, a decreasing tube outside diameter, or both. Further, a variable aperture die can be used to vary tubing diameter and/or wall thickness.

Figure 5:
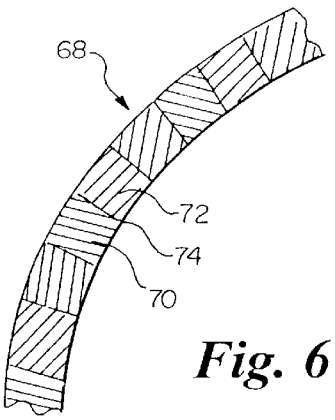
FIG. 5 is a fragmentary, transverse, cross-sectional view of a tube wall section formed of moderately fused strands, the wall surface having lost much of the original strand round surface shape.

Referring now to FIG. 5, another embodiment of the invention is illustrated in a tube wall section 68 having a higher degree of fusing or bonding than the tube wall illustrated in FIG. 3. Tube wall section 68 includes a first strand 70 and a second strand 72 which are fused along a common boundary 74. The embodiment of FIG. 5 has more contact area between strands than the embodiment of FIG. 3 due to the higher degree of fusing or melting. The strand materials of the embodiment of FIG. 5 have also been made to flow or deform under heat more than the embodiment of FIG. 3, as can be seen from the loss of the individual strand shapes and the gain of the shape of the annulus formed between the inner circular mandrel and the outer circular die. The strands of FIG. 5, while more highly fused than the strands of FIG. 3, can still retain their separate characteristics and have not diffused into each other to any appreciable degree.

Figure 6:
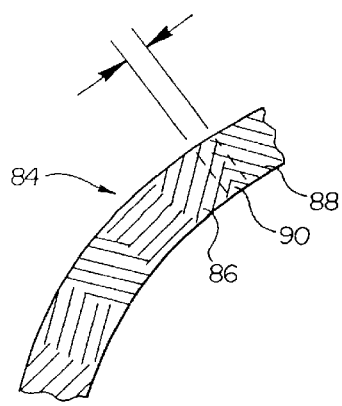
FIG. 6 is a fragmentary, transverse, cross-sectional view of a tube wall formed of highly fused strands that have diffused into one another.

Referring now to FIG. 6, a highly fused tube wall section 84 is illustrated including a first strand region 86 and a second strand region 88. In the highly fused embodiment illustrated, first region 86 and second region 88 have material of adjacent strands diffused into one another in a diffused, mixed inter-strand region 90. In this region the adjacent strands have melted or diffused into each other, further strengthening the inter-strand bond. In the embodiments illustrated in FIGS. 5 and 6, the high degree of melting has given the tube surfaces the characteristics of the inner mandrels and the outer die within which the strands were disposed during processing.

Referring now to FIG. 7, a tube 76 is illustrated having a plurality of strands 78 embedded within an adhesive or filler polymer 80. The use of an adhesive or polymer can result in a smoother outer surface 82, where the outer surface loses much of the surface structure of the individual strands making up the tube. As discussed with respect to FIG. 4, mandrels 62, 64, and 66 can be used to form lumens 56, 58, and 60. The use of a filler or adhesive allows use of strand materials that may not readily bond directly to one another, but have properties desirable to include in the tube. One example of such a strand material is metallic wire, which may be difficult to fuse directly to adjacent polymeric strands in the embodiment of FIG. 4. The use of a polymeric filler or adhesive allows the metallic wires to be embedded in a matrix adjacent to polymeric strands without requiring the direct bonding of the adjacent strands.

Figure 8:
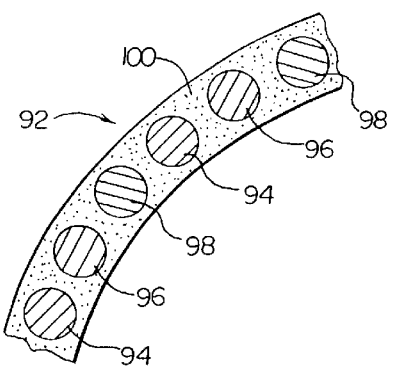
FIG. 8 is a fragmentary, transverse, cross-sectional view of a tube wall section formed of strands bonded together with the aid of a filling and/or bonding agent.

Referring now to FIG. 8, a tube wall section 92 similar to the wall of tube 76 is illustrated. Tube wall section 92 includes first strands 94, second strands 96, and third strands 98, all embedded within an adhesive or filler material 100. Strands 94, 96, and 98 preferably have different properties adjacent strands.

Figure 9:
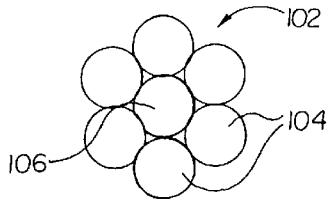
FIG. 9 is a transverse, cross-sectional view of a strand formed of a plurality of filaments.

Referring now to FIG. 9, a strand 102 is illustrated with strand 102 itself being formed of multiple filaments. The multi-filament strand 102 is formed of several filaments including outer filaments 104 and an inner filament 106. In one embodiment inner filament 106 is a metallic wire and outer filaments 104 are formed of polymeric material. In another embodiment, inner filament 106 is formed of a strong polymer such as Kevlar™, and outer filaments 104 are formed of polymers more amenable to bonding with other filaments. FIG. 9 thus illustrates that the strands of the present invention can be formed of multiple strands or filaments.

Strands are preferably formed of polymeric materials suitable for heat bonding to one another. In one embodiment, strands include fibers. In embodiments using an adhesive, bare fibers may be suitable. In embodiments relying on heat bonding, polymer covered fibers are preferred. In some embodiments, metallic wires form at least one strand in each tube. In embodiments utilizing heat fusing between strands, polymeric covered metallic wires are preferred. Polymeric materials which make up the strands can include, alone or in combination, polyethylene, nylons, polyolefins, polyamides and/or polyesters.

The present invention thus includes bonding multiple strands together to form a tube having a lumen or lumens therethrough. As previously discussed, one bonding method uses heat to fuse adjacent strands together. Fusing can include heating from within using a mandrel and heat from without using a heated die. One fusing method utilizes a die having a smaller outlet inside diameter than inlet inside diameter. One such decreasing conically tapered die has an inlet which can serve to gather, heat, and compress the strands about a central mandrel. The strands thus become at least softened and amenable to fusing to adjacent strands. Some embodiments include only a small degree of compression, resulting in strands retaining much of their original shape, as illustrated in FIG. 3. Other embodiments include a high degree of compression and a squeezing and/or flow of the strands between inner mandrel and outer die, as illustrated in FIG. 5. Still other embodiments utilize a high degree of compression or heat and flattening of the strands, such that strands have a width nominally several times the original strand width. In one such embodiment, the strand width is increased about fourfold. In another such embodiment, the strand width is increased about eightfold. The flattening of the strand allows use of fewer strands to completely form a tube outer surface. By way of illustration, FIG. 4 uses thirty-two (32) strands to form a tube. If the strands in FIG. 4 were flattened to increase their width fourfold, then nominally only eight strands would be required to form the tube wall.

One alternative use of the present invention is for forming an angioplasty balloon envelope, which is essentially a tubular member. A balloon envelope can be formed using multiple strands which are fused or bonded to adjacent strands. One balloon envelope utilizes a low degree of compression and a large number of strands to form the envelope circumference. Another balloon envelope utilizes a high degree of compression and a small number of strands to complete the circumference. Still another balloon envelope utilizes strands having large diameters and some adjacent strands have small diameters, coupled with a high degree of compression to flatten the large strands to cover a large amount of the envelope circumference. The large and small diameter strands can be alternated in various patterns to achieve the desired dispersion of small strands within a tube or balloon wall.

One embodiment includes elastic strands dispersed about the balloon envelope circumference. One such embodiment includes elastic strands longitudinally dispersed at 90° intervals about the balloon circumference. Under applied inflation fluid pressure, the envelope regions corresponding to the elastic strands inflate, but upon deflation, the more elastic longitudinal regions will preferentially contract inward relative to the less elastic regions disposed therebetween. The more elastic regions thus form preferential folding regions dispersed at regular intervals about the balloon envelope. The less elastic regions can be either compliant or non-compliant, depending on the desired balloon characteristics. The preferential folding regions can form a deflated balloon having a smaller profile than a balloon having random folding. For example, a balloon having longitudinal elastic regions disposed 90° apart may provide a deflating balloon having four wings disposed between the elastic regions. A deflated balloon having four outwardly disposed wings will have a smaller profile than a similar balloon having a flattened or pancaked balloon having only two outwardly disposed wings. The smaller profile can provide an advantage in retracting the balloon through body vessels after use.

Another embodiment of the invention includes at least one longitudinal strand differing from the adjacent strands, resulting in a weaker longitudinal strip along the balloon envelope. The weaker longitudinal strip can be used to deal with accidental overpressure situations, where the balloon is inadvertently supplied by the user with fluid pressure greater than the burst strength of the balloon. The weaker strip should fail first and direct any balloon tear along the direction of the weaker strip.

Another embodiment of the invention can be explained with reference again to FIGS. 1 and 2. This embodiment includes a spiral or helical orientation of the strands about a central mandrel prior to entry into the die. Spools containing the strands can be mounted on a rotating ring or wheel and the ring rotated about the central mandrel. The rotation can impart a helically wound set of strands which can be bonded together in the die as previously discussed. This method can be used in conjunction with strands including metallic wires within. One method runs the helically wound tube through a second die, with a second series of strands being wound in a sense opposite to the first set of strands. For example, the first pass can form a tube of clockwise wound strands fused together and the second pass can form a tube having counter-clockwise strands fused together over the clockwise wound strands. The resulting tube provides enhanced tortional strength relative to a tube including strands wound only in one direction.

After bonding within a die, a tube formed according to the present invention can be further processed. One processing step includes winding a strand or strands about the newly formed and bonded tube. For example, strands to strengthen the tube can be helically wound or braided about the tube. In particular, the collapse strength of the tube can be increased by winding a helical coil or braid about the tube.

Another processing step includes coating the tube with metal. For example, the tube formed of multiple strands can be coated with a metallic coating using sputter coating or vacuum deposition techniques well known to those skilled in the art. The multi-strand tube can be passed through a conventional extruder and covered with polymer. In one method, the tube is drawn while the strands are still soft from heating so as to orient the polymers in the longitudinal direction and increase the tube strength. In another method, the individual strands are pulled to orient the polymer while the strands are fed into a die.

As previously discussed, heating strands and causing the strands to fuse is a preferred method for bonding strands together. One method supplies sufficient heat to melt only the exterior of the strands while another method melts much of the strand interior. Fusing the strands together is accomplished in one method using a plasma energy source. In another method, the strands are coated with an adhesive or solvent prior to entering a die. The adhesive or solvent is carried into the die with the strands and acts to bond the strands within the die. Alternatively, the strands can be plasma treated prior to contacting each other, wherein subsequent contact results in adhesion.

One class of methods utilizes UV curable material to bond strands together. One of these methods includes coating individual strands with UV curable material, which is carried into a die and cured with UV light which can be supplied either prior to or within the die. One method varies the amount of UV curable material over the length of the tube to vary the degree of cross-linking and the resulting stiffness. For example, one method utilizes strands having an increasing amount of UV curable material over the strand length. For example, the amount of UV curable material can be varied from ten (10) to twenty (20) weight percent over the strand length. After exposure to UV light, the portion of the strand having 20% UV curable material has a greater cross-linked stiffness than the portion having only 10% UV curable material. The amount of UV curable material can effect both the inter-strand bonding and the stiffness of the strand itself after curing. In an alternative embodiment, the flow of adhesive can be stopped to individual or multiple ports at selected axial positions on the tubing. This results in a port or opening between the strands through the tubing wall. The port may be used to dispense fluids.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method for making medical tubing comprising the steps of:

providing a plurality of strands;

aligning said strands into a substantially tubular shape, wherein said strands are substantially longitudinally oriented into a single layer; and bonding said strands together.

2. A method for making medical tubing as recited in claim 1, wherein said substantially tubular shape includes at least one lumen.

3. A method for making medical tubing as recited in claim 1, wherein said bonding step includes applying heat to said strands.

4. A method for making medical tubing as recited in claim 1, wherein said aligning step includes passing said strands through an aligner having at least one inner mandrel.

5. A method for making medical tubing as recited in claim 4, wherein said inner mandrel is heated and said bonding step includes applying heat to said strands.

6. A method for making medical tubing as recited in claim 1, wherein said bonding step includes solvent welding.

7. A method for making medical tubing as recited in claim 1, wherein said bonding step includes embedding said strands in a filler.

8. A method for making medical tubing as recited in claim 1, wherein said bonding step includes embedding said strands in an adhesive.

9. A method for making medical tubing as recited in claim 8, wherein at least one port is formed through a wall of said tubing by omission of said adhesive.

10. A method for making medical tubing as recited in claim 1, wherein said bonding step includes plasma etching said strands.

11. A method for making medical tubing as recited in claim 1, wherein said aligning step includes passing said strands through a die and said fusing step includes injecting adhesive onto said strands.

12. A method for making medical tubing as recited in claim 1, wherein at least one of said strands includes polymer formed over a metallic core.

13. A method for making medical tubing as recited in claim 1, wherein said strands include a UV curable polymer and said fusing steps includes exposing said strands to UV light.

14. A method for making medical tubing as recited in claim 13, wherein said strands have a length and said UV curable polymer is varied over said length for varying the degree of cross-linking of said strands to one another.

* * * * *